United States Patent [19]
Glenday et al.

[11] Patent Number: 5,622,675
[45] Date of Patent: Apr. 22, 1997

[54] SAMPLE SEGMENT

[75] Inventors: Ronald C. Glenday, Fullerton; David L. Goodale, Yorba Linda; Steven D. Mack, Mira Loma, all of Calif.

[73] Assignee: Beckman Instruments, Inc., Fullerton, Calif.

[21] Appl. No.: 489,793

[22] Filed: Jun. 13, 1995

Related U.S. Application Data

[63] Continuation of Ser. No. 71,831, Jun. 3, 1993, abandoned, which is a continuation of Ser. No. 48,716, Apr. 16, 1993, abandoned.

[51] Int. Cl.$^6$ ........................................ B01L 3/00
[52] U.S. Cl. ................. 422/102; 422/63; 436/43; 436/47; 436/48
[58] Field of Search ..................... 422/63, 64, 65, 422/99, 102, 104; 436/43, 47, 48; 204/451, 601, 602, 604

[56] References Cited

U.S. PATENT DOCUMENTS

| | | | |
|---|---|---|---|
| 3,441,383 | 4/1969 | Moore et al. | 427/102 |
| 3,536,449 | 10/1970 | Astle | 436/179 |
| 3,540,858 | 11/1970 | Rochte et al. | 422/101 |
| 3,554,705 | 1/1971 | Johnston et al. | 422/61 |
| 3,680,967 | 8/1972 | Engelhardt | 356/246 |
| 3,713,771 | 1/1973 | Taylor et al. | 436/48 |
| 3,713,985 | 1/1973 | Aslte | 435/33 |
| 4,287,155 | 9/1981 | Tersteeg et al. | 422/64 |
| 4,298,570 | 11/1981 | Lillig et al. | 422/64 |
| 4,695,430 | 9/1987 | Coville et al. | 422/65 |
| 4,900,513 | 2/1990 | Barker et al. | 422/64 |
| 4,908,320 | 3/1990 | Zakowski et al. | 436/45 |
| 5,005,721 | 4/1991 | Jordan | 422/102 X |
| 5,051,238 | 9/1991 | Umetsu et al. | 422/64 |
| 5,145,646 | 9/1992 | Tyranski | 422/102 |
| 5,228,960 | 7/1993 | Liu et al. | 204/451 |
| 5,356,525 | 10/1994 | Goodale et al. | 204/602 |

FOREIGN PATENT DOCUMENTS

| | | |
|---|---|---|
| 0415307 | 8/1990 | European Pat. Off. . |
| 0329579 | 2/1989 | France . |
| 0204109 | 4/1986 | Germany . |
| 0100663 | 7/1983 | United Kingdom . |
| WO9220448 | 11/1992 | WIPO . |

*Primary Examiner*—Jill Warden
*Assistant Examiner*—Maureen M. Wallenhorst
*Attorney, Agent, or Firm*—William H. May; Gary T. Hampson

[57] ABSTRACT

A sample segment including a body and wells formed therein, selected wells including a flat exterior surface surrounding a tapered end. The sample segment may retain selected reagents, and a sealing cover is held by ribs, stretched and pressed against raised bosses formed around the well openings to provide a sure seal. The bosses are discontinuous between adjacent wells. Selected wells may contain a free mixing element for enhanced mixing. The segment is uniquely adapted for automated handling and processing.

42 Claims, 2 Drawing Sheets

SAMPLE SEGMENT

RELATED APPLICATION

This application is a continuation of U.S. patent application Ser. No. 08/071,831, filed Jun. 3, 1993, now abandoned, which is a continuation of U.S. patent application Ser. No. 08/048,716, filed Apr. 16, 1993 and abandoned.

The present application is related to the following applications that are commonly assigned and fried concurrently herewith, and which are incorporated herein by reference:

U.S. patent application Ser. No. 08/072,202, filed Jun. 3, 1993 and now U.S. Pat. No. 5,356,525 issued on Oct. 18, 1994, entitled "Sample Handling System", filed in the names of David L. Goodale and Steven D. Mack, which is a continuation of U.S. patent application Ser. No. 08/048,708, filed Apr. 16, 1993 now abandoned; and U.S. patent application Ser. No. 08/071,832, filed Jun. 3, 1993 and now U.S. Pat. No. 5,417,925 issued on May 23, 1995, entitled "Capillary and Capillary Retaining System", filed in the names of David L. Goodale and George I. Reeves, which is a continuation of U.S. patent application Ser. No. 08/048,709, filed Apr. 16, 1993, now abandoned.

FIELD

The present invention relates to the field of sample and reagent carrying devices, and more particularly to sample carrying devices useful in automated analyzers.

BACKGROUND

Various forms of sample carrying devices are known in the art. For example U.S. Pat. No. 3,713,985 (Astle) describes a testing device which includes a plurality of receptacles or wells interconnected integrally by a horizontal support member. The device includes vertical support members or legs and several of the receptacles contain a range of biological control reagents in an essentially dry form. The receptacles are sealed by a seating material such as plastic film or aluminum foil by heat or pressure.

Still other fonns of devices are known for use on automated analyzers. As an example, U.S. Pat. No. 4,298,570 (Lillig) describes a tray section that has a plurality of webs. The tray section is carded by a turntable, which also receives sample containers. A sample is pipetted from a sample container into a well in the tray section, where additional dilutions of the sample are made. The diluted samples are then taken by an automated pipette to a reaction cell for analysis.

As described in the concurrently filed application (Ser. No. 08/048,708 filed Apr. 16, 1993, now abandoned entitled "Sample Handling System", and identified above (and which is not admitted to be prior art with respect to the present invention by its mention in this Background), there is disclosed in such application a novel and inventive system which is useful with a sample device or segment that is moved about by the system to accomplish the required analysis. However, neither the Lillig or Astle device is suitable for use with such a system because, for example, neither device includes structure that could be readily gripped by a transport apparatus.

Further, such system is adapted to be used in a capillary electrophoresis analyzer that performs, for example, immunosubstraction capillary electrophoresis analyses. Such analyses require reagents, including liquid reagents, to be stored in the device. Although Astle describes a sealing material, sealing of the type of Astle tends to allow leakage between adjacent reservoirs, particularly with a liquid reagent, and thus would be unsatisfactory for analytical techniques such as capillary electrophoresis, particularly where adjacent reagents are different.

Reagent mixing within the reservoirs of a sample device is also desirable as, for example, in an immunosubtraction capillary electrophoresis analysis. Both the Lillig and Astle devices, however, would require, for example, an external stirring device to accomplish effective mixing of the reagents.

Thus, there is a need for a sample-carrying device that is suitable for use in an analyzer wherein the sample-carrying device is transported within the analyzer to accomplish a desired analysis. There is also a need for a sample carrying device that can be more surely sealed to prevent leakage of reagents, such as liquid reagents, between adjacent reservoirs. There is also a need for a sample carrying device with improved mixing capabilities within the device reservoirs.

SUMMARY OF THE INVENTION

The sample segment of the present invention overcomes the limitations described above. In one form of the present invention, the sample segment includes a body and a plurality of wells formed in the body. At least two of the wells include exterior surfaces around the exterior of such wells, formed at predetermined positions with respect to such wells. For example, the surfaces may be flat and may be disposed substantially midway along an interior axial dimension of such wells, or may be between a flange and an exterior end of such wells, or may be formed such that most of the interior volumes of such wells is between a plane defined by the surfaces and the openings of such wells.

Additionally, a plane defined by the surfaces can be essentially perpendicular to central axes of the wells. The exterior ends of the wells around which the surfaces are formed are reduced. The reduced portion may be tapered and the end itself may be rounded. The interior walls of the wells may also be tapered.

Additionally, the sample segment may include curved opposite edges and the wells may be formed along an arc defined between such edges.

In another aspect of the present invention, the sample segment may include a body, a plurality of wells, and a raised boss on the body around the opening of one of the wells. Bosses may be formed around additional ones or all of the wells, and a cover may be applied to the bosses to seal the wells. The cover may be a label and a reagent may be in the wells before sealing.

In yet another aspect of the present invention, a sample segment may include a body, a plurality of wells, and a mixing element disposed in at least one of the wells. The mixing element may take the form of a length of wire.

Further, a sample segment in accordance with the present invention may include various combinations of the features just described.

BRIEF DESCRIPTION OF THE DRAWINGS

These and other features and advantages of the present invention will be apparent from the drawings in which.

DETAILED DESCRIPTION

Figure 1:
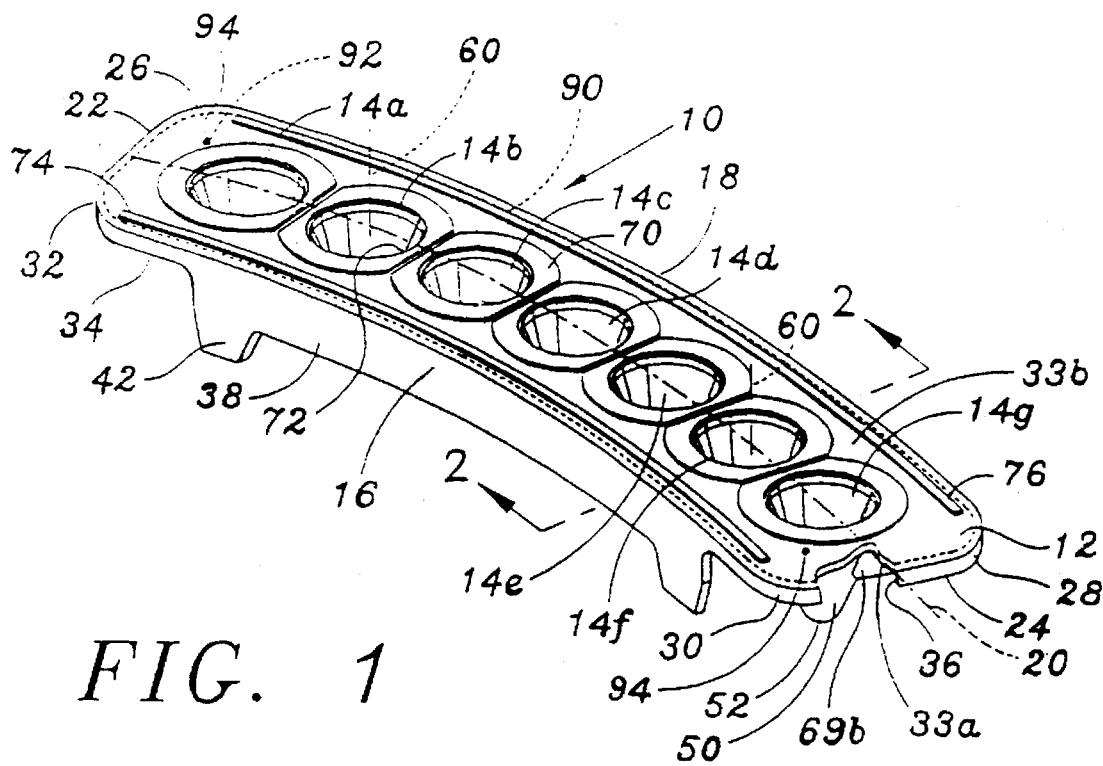
FIG. 1 is a perspective view of a sample segment in accordance with the present invention.

With reference to FIG. 1, a sample segment 10 in accordance with the present invention is defined by a body in the form of a flange 12 and a plurality of wells 14. The flange 12 is generally arcuate, having curved opposite edges 16, 18 and an arcuate center line 20. The flange 12 has ends 22, 24 that are generally perpendicular to the center line 20 and rounded corners 26, 28, 30, 32 and first and second surfaces 33a, 33b.

Depending lips 34, 36 arid depending sides 38, 40 are formed around the periphery of the flange 12, the lips 34, 36 being proximate the ends 22, 24 and the sides 38, 40 being formed along most of the lengths of the edges 16, 18. Each of the sides 38, 40 includes two legs 42 suitable for supporting the sample segment 10 on a flat surface.

In the embodiment disclosed herein, seven wells 14, identified individually as wells 14a–14g in FIG. 1, are defined in the sample segment 10. Each well 14 lies on the arcuate center line 20 and defines a round opening 44 (FIG. 2) in the flange 12 and has an interior volume 46 defined by a tapered interior wall surface 47 and a rounded interior bottom surface 48. The exterior surfaces 50 of all but two of the wells 14 are similarly tapered and have similarly rounded exterior ends 52. In the specific embodiment disclosed herein, the interior volume 46 is about 205 µl, although other volumes may be suitable.

The two wells 14b, 14f, which each are the second well from the respective ends 22, 24, have an exterior cylindrical wall portion 54 proximate the flange 12, the wall portion 54 defining an annular flat surface or shoulder 56. The flat surfaces 56 on the shouldered wells 14b, 14f together define a plane 58 that is generally parallel to the flange 12. Thus, the flat surfaces 56 are generally perpendicular to central axes 60 of the wells 14b, 14f. The axis 60 also defines an interior axial dimension 61 between the top of the round opening 44 (as oriented in FIG. 2) and the bottom surface 48. As seen, for example, in FIG. 2, most of the interior volume 46 of each of the shouldered webs 14b, 14f is between the plane 58 and the openings 44 for such wells. The remaining lower exterior wall 62 of the shouldered wells 14b, 14f is similar to the other webs such as shouldered well 14g shown in FIG. 1, having a tapered or reduced wall portion 64 and a rounded exterior end or end portion 66. As is also seen with reference to FIG. 2, the flat surfaces 56 are between the first surface 33a and the exterior end 66, and the flat surfaces 56 can also be described as substantially midway along the interior axial dimension 61.

Reinforcing ribs 68 (FIGS. 2, 3) are formed between the flange 12, wells 14 and depending sides 38, 40, adding strength and rigidity to the sample segment 10. Indexing ribs 69a, 69b (FIG. 1,3) are formed proximate the ends 22, 24 between the flange 12, lips 34, 36 and the end wells 14a, 14g, and are thus generally triangular in shape. The indexing ribs 69a, 69b are used to locate or index the sample segment 10 with respect to supports on an analyzer on which the sample segment 10 may be used as is described with reference to FIG. 4 below.

Each well 14 includes an annular raised boss 70 formed around the openings 442 Each of the bosses 70 is separate and discontinuous from adjoining ones of the bosses 70 by means of grooves 72. Raised ribs 74, 76 are proximate the edges 16, 18, respectively, the ribs 74, 76 projecting from the flange 12 more than the bosses 70.

Figure 2:
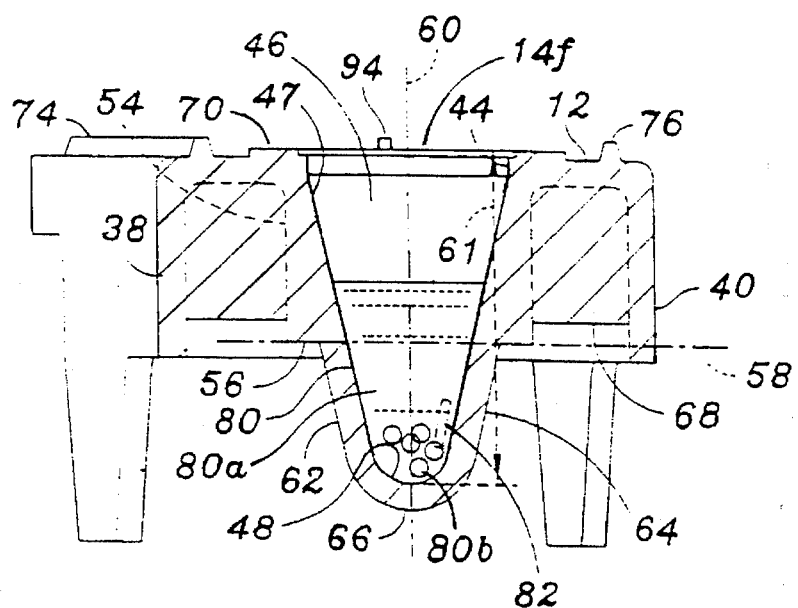
FIG. 2 is a section view of the sample segment of FIG. 1 taken along line 2—2 thereof.
Figures 3, 4:
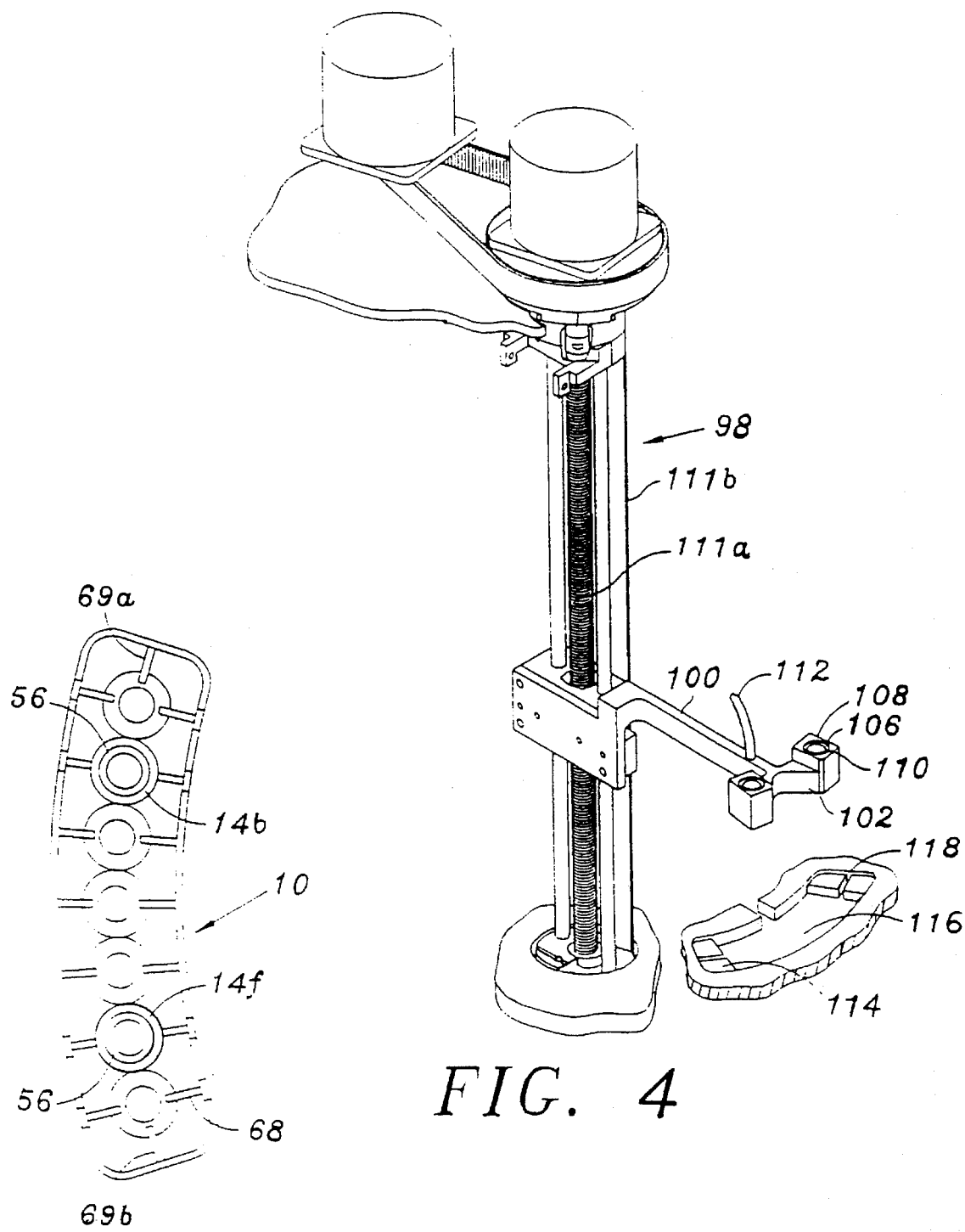
FIG. 3 is a bottom view of the sample segment of FIG. 1.
FIG. 4 is a simplified perspective view of a transport means with which the sample segment of FIG. 1 may be used.

Selected ones or all of the wells 14 may carry a reagent 80, shown for illustration purposes in the cross-section view of well 14f in FIG. 2. The reagents 80 may take the form of a liquid component 80a and a solid support component 80b as may be useful, for example, in capillary electrophoretic immunosubtraction. Such a technique is disclosed in U.S. patent application Ser, No. 07/916,313, filed Jul. 17, 1992 U.S. patent application Ser. No. 08/071,832, filed Jun. 3, 1993 and now U.S. Pat. No. 5,417,925 issued on May 23, 1995, entitled "Analysis of Samples by Capillary Electrophoretic Immunosubtraction," in the name of Liu, et al. and which is incorporated by reference herein. Other forms of reagents for other types of analysis will be apparent to those skilled in the art. Selected ones or all of the wells 14 may also carry a mixing element 82, formed in this embodiment from round nickel chromium wire. The mixing element 82 is about 0.040 inch in diameter and about 0.125 inch long in this particular embodiment, but other dimensions may also be suitable. Preferably, each of the wells 14 that includes a reagent 80 also includes a mixing element 82, although such a relationship may not be necessary according to the mixing requirements for the reagent 80. Further, a mixing element 82 could be contained in a well 14 which contains no prepackaged reagents 80.

The sample segment 10 may include a sealing cover such as a label 90. The label 90 may be a laminate of metal foil and plastic film and is formed to cover the flange 12, and has alignment holes 92 which are sized to receive locating pins 94 on the flange 12 proximate the wells 14a, 14g. The label 90 may be printed on the exposed side and may carry, for example, human and/or machine readable characters.

The sample segment 10 may be formed, for example, from HDPE via injection molding and is prepared by adding the deskred reagents 80 and mixing elements 82. The label 90 is aligned by means of the locating pins 94. Preferably, the label 90 is first pressed across the ribs 74, 76 and affixed or "tacked" to the ribs 74, 76, such as by heat sealing to hold the label 90 in place. The label 90 is then pressed against and heat sealed to the bosses 70. Because the ribs 74, 76 project further from the flange 12 than the bosses 70, this sequence causes the label 90 to be slightly stretched as it is pressed and sealed against the bosses 70, ensuring that the label 90 is not wrinkled or otherwise deformed as it is fixed to the sample segment 10 and improving the seal between the label 90 and the bosses 70. The heat sealing of the label 90 is best accomplished when the plastic film side of the label 90 is against the plastic material from which the sample segment 10 is formed.

The sample segment 10 is useful with an automated transport means which receives and removably retains the sample segment 10 by means of the flat surfaces 56 and exterior walls 62 on the wells 14b, 14f. Such an automated transport means 98 (FIG. 4) may include, for example, an ann 100 with forks or projections 102 at one end thereof. The projections 102 carry flexible boots 106 that include sealing upper rims 108 and interiors 110 shaped to conform to the exterior walls 62. The interiors 110 are connected to tubing 112 which is in turn connected to a controllable source of vacuum. The boots 106 and interiors 110 are spaced to align with the axes 60 of the wells 14b, 14f. The automated transport means 98 also may include means, such as a lead screw 111a and spindle 111b for rotational and vertical displacement of the ann 100.

The automated transport means may also include holding means for the sample segment 10 having supports 114 upon which the ends 22, 24 are supported with an open area 116 through which the projections 102 can be raised. Slots 118 in the supports 114 are spaced and sized to receive the indexing ribs 69a, 69b, thus indexing or accurately positioning the sample segment 10 with respect to the open area 116 and thus the automated transport means 98. To retrieve and removably retain the sample segment 10, the sample segment 10 is disposed on the holding means and the boots are aligned with the wells 14b, 14f. The arm 100 is moved upwardly to receive the exterior walls 62 and flat surfaces 56. Vacuum is applied via the tubing 112, holding the sample segment 10 in place. Thus, by moving the arm 100, the sample segment 10 may be transported about, for example, for addition and removal of fluid via a probe (not shown) and the like. Further, the arm 100 may describe a motion wherein the arm 100 is rotated horizontally about a vertical axis, the boots 106 following a constant radius path about the vertical axis. Preferably, an arc of such a path matches the arcuate center line 20 of the flange 12.

The arm 100 with the sample segment 10 retained thereon may be agitated, for example, by being vibrated to achieve mixing of the well 14 contents. The mixing element 82, during such agitation, creates a thorough and rapid mixing action, the element 82 climbing the interior surface 47 as the vortexing action is induced by such agitation. This provides a scraping action that promotes a thorough mixing of well 14 contents.

Conversely, the sample segment 10 can be deposited at the supports 114 my lowering the arm 100 through the open area 116 until the sample segment 10 is indexed by the indexing ribs 69a, 69b engaging the slots 118 and the sample segment 10 comes to rest on the supports 114, releasing the vacuum, and further lowering the arm 100.

Thus, a sample segment 10 in accordance with the present invention is particularly and uniquely adapted for transport by means of automatic transport means. A sample segment 10 in accordance with the present invention provides a unique and leak-resistent seal over the wells 14 thereof. Further, a sample segment in accordance with the present invention includes a mixing element that provides improved and consistent mixing of reagents that may be contained within or added to the wells 14. These advantages are evident from these individually inventive aspects of the present invention, and further advantages are evident by combinations of such aspects.

While the segment 10 is referred to herein as a sample segment, it is to be recognized that the segment 10 is not to be limited merely to samples, but is useful for various reagents that may be used in analysis. Thus, the word "sample" is to be read and interpreted broadly to include but not be limited to, for example, liquid as well as solid patient samples, reagents, diluents, buffers, and the like, and solutions thereof.

The present invention is not to be limited to the particular embodiment described herein but shall be accorded the full scope of the appended claims and all equivalents thereof.

We claim:

1. A sample segment for use with an automated analyzer having transport means comprising an arm and at least two bores, the sample segment comprising:

a body having an upwardly facing surface and a downwardly facing surface; and a plurality of wells integrally formed as inseparable components of the body, at least two of the wells being transport wells and having an interior axial dimension defined by exterior surface walls and including exterior annular flat surfaces around the exterior walls of said transport wells, the flat surfaces facing downwardly in a direction parallel to said axial dimension and being disposed substantially midway along the interior axial dimension, wherein the exterior surface walls of the transport wells include exterior rounded ends and the exterior surface walls of the transport wells between the flat surface and the ends of the wells are reduced and tapered relative to the exterior surface walls between the opening of the wells and the flat surfaces, wherein the sample segment can be directly engaged by the transport means by each bore receiving one of said transport wells with the corresponding flat surface being directly engaged by the transport means.

2. A method of sample and reagent transport in an automated analyzer having transport means comprising an arm and at least two bores, the method comprising the steps of:

(a) providing a sample segment as claimed in claim 1;

(b) engaging the sample segment by the transport means by each bore receiving one of the transport wells with the corresponding flat surface being directly engaged by the transport means;

(c) moving the sample segment by moving the arm; and (d) disengaging the sample segment from the arm.

3. The method of claim 2 wherein the transport means further comprises a support for the sample segment, and wherein the step of disengaging the sample segment from the arm further comprises placing the sample segment on the support.

4. The method of claim 2 wherein the transport wells of the sample segment include inner tapered walls.

5. The method of claim 2 wherein for each of the transport wells of the sample segment, at least 50% of the interior volume of the well is defined by the flat surface of the exterior wall of the well and the opening of the well.

6. A sample segment for use with an automated analyzer having (i) a support for the segment, the support having a slot therein, and (ii) transport means for transporting the segment comprising an arm with at least two bores, the sample segment being of unitary construction and comprising:

a flange having a first upwardly facing surface and a second downwardly facing surface;

a plurality of wells integrally interconnected with the flange and having exterior surfaces and exterior ends proximate the first surface of the flange;

a first indexing rib interconnecting the second surface of the flange and the exterior surface of a first selected well;

at least two of the wells being transport wells and including an annular flat surface formed about the exterior surfaces of said transport wells, the flat surfaces facing downwardly in a direction perpendicular to said flange and being positioned between the first surface of the flange and the exterior ends of said transport wells;

the sample segment being directly engagable by the transport means by each bore receiving one of said transport wells having said flat surfaces with the corresponding flat surface being directly engaged by the transport means, and wherein the transport means can place the sample segment on the support with the slot receiving the indexing rib.

7. A sample segment as in claim 6 wherein the flat surfaces are substantially midway between the first surface of the flange and the exterior ends of said transport wells.

8. A sample segment as in claim 6 wherein the sample segment includes a second indexing rib interconnecting the second surface of the flange and the exterior surface of a second selected well.

9. A sample segment for use with an automated analyzer having transport means comprising an arm and at least two bores, the sample segment comprising:

a body having an upwardly facing surface and a downwardly facing surface;

a plurality of wells integrally formed as inseparable components of the body, each of the wells having an opening in an upwardly facing surface of the body and defining an interior volume, at least two of the wells being transport wells and having an interior axial dimension defined by exterior surface walls and including exterior flat annular surfaces around the exterior walls of said transport wells, the flat surfaces facing downwardly in a direction parallel to said axial dimension and being disposed along the exterior walls of said transport wells such that, for each of said transport wells, at least 50% of the interior volume of the well is between a plane defined by the flat surface and the opening of the well, wherein the exterior surface walls of the transport wells include exterior rounded ends and the exterior surface walls of the transport wells between the flat surface and the ends of the wells are reduced and tapered relative to the exterior surface walls between the opening of the wells and the flat surfaces, wherein the sample segment can be directly engaged by the transport means by each bore receiving one of said wells having said exterior flat surfaces with the corresponding flat surface being directly engaged by the transport means.

10. A sample segment as in claim 9 wherein the transport wells include inner tapered walls.

11. A sample segment for use with an automated analyzer having transport means comprising an arm and at least two bores, the sample segment comprising:

a body having an upwardly facing surface and a downwardly facing surface;

a plurality of wells integrally formed as inseparable components of the body, each of the wells having an opening in an upwardly facing surface of the body and defining an interior volume, at least two of the wells being transport wells and having an interior axial dimension defined by exterior surface walls and including exterior annular flat surfaces around the exterior walls of said transport wells, the annular surfaces facing downwardly in a direction parallel to said axial dimension and being disposed on the exterior walls of said transport wells such that, for each of said transport wells, at least 50% of the interior volume of the well is between a plane defined by the flat surface and the opening of the well, wherein the exterior surface walls of the transport wells include exterior rounded ends and the exterior surface walls of the transport wells between the flat surface and the ends of the wells are reduced and tapered relative to the exterior surface walls between the opening of the wells and the flat surfaces, wherein the sample segment can be directly engaged by the transport means by each bore receiving one of said wells having said exterior annular flat surface with the corresponding annular flat surface being directly engaged by the transport means; and a raised boss on the upwardly facing body surface around the opening of each of the wells.

12. A sample segment as in claim 11 wherein the sample segment further includes a plurality of raised bosses and includes areas that are not raised between adjacent bosses.

13. A sample segment as in claim 12 wherein the sample segment includes curved opposite edges and the wells are formed in an arc between the curved opposite edges.

14. A sample segment as in claim 13 wherein the segment further includes raised arcuate ribs proximate the curved opposite edges, and a cover that is applied over the ribs and bosses and is sealed to the bosses.

15. A sample segment as in claim 14 wherein the dimension by which the ribs are raised with respect to the upwardly facing body surface is greater than the dimension by which the bosses are raised with respect to the upwardly facing body surface and the cover is fixed across the ribs before a label is pressed and sealed against the bosses.

16. A sample segment as in claim 15 wherein the cover is a label including readable characters thereon.

17. A sample segment as in claim 16 wherein the label is heat sealed to the bosses.

18. A sample segment for use with an automated analyzer having transport means comprising an arm and at least two bores, the sample segment comprising:

a body having an upwardly facing surface and a downwardly facing surface;

a plurality of wells integrally formed as inseparable components of the body, each of the wells having an opening in an upwardly facing surface of the body and defining an interior volume, at least two of the wells being transport wells and having an interior axial dimension defined by exterior surface walls and including exterior annular flat surfaces around the exterior of said transport wells, the annular surfaces facing downwardly in a direction parallel to said axial dimension and being disposed on the exterior walls of the wells, wherein the exterior surface walls of the transport wells include exterior rounded ends and the exterior surface walls of the transport wells between the flat surface and the ends of the wells are reduced and tapered relative to the exterior surface walls between the opening of the wells and the flat surfaces, wherein the sample segment can be directly engaged by the transport means by each bore receiving one of said wells having said exterior annular flat surface with the corresponding annular flat surface being directly engaged by the transport means;

at least one of the wells containing a reagent; and a mixing element disposed in the well containing the reagent.

19. A sample segment as in claim 18 wherein the annular flat surfaces are disposed on the exterior walls of the transport wells such that, for each of said transport wells, at least 50% of the interior volume of the well is between a plane defined by the flat surface and the opening of the well.

20. A sample segment as in claim 18 wherein at least two of the wells contain a reagent, each well that contains a reagent includes a mixing element and a cover sealed over the opening of the well.

21. A sample segment as in claim 18 wherein the sample segment includes a raised annular boss on the upwardly facing body surface around the opening of at least the well containing the reagent.

22. A sample segment as in claim 21 wherein the sample segment includes curved opposite edges and the wells are formed in an arc between the curved opposite edges.

23. A sample segment as in claim 22 wherein the segment further includes a plurality of raised bosses and raised arcuate ribs proximate the curved opposite edges, and a label that is applied over the ribs and bosses and is sealed to the bosses.

24. A sample segment as in claim 23 wherein the dimension by which the ribs are raised with respect to the upwardly facing body surface is greater than the dimension by which the bosses are raised with respect to the upwardly facing body surface and the label is stretched across the ribs before the label is pressed and sealed against the bosses.

25. A sample segment for use with an automated analyzer having transport means comprising an arm and at least two bores, the sample segment comprising:

a body having an upwardly facing surface and a downwardly facing surface;

a plurality of wells integrally formed as inseparable components of the body, each of the wells having an opening in an upwardly facing surface of the body and defining an interior volume, at least two of the wells being transport wells and having an interior axial dimension defined by exterior surface walls and including exterior annular flat surfaces around the exterior walls of said transport wells, the flat surfaces facing downwardly in a direction parallel to said axial dimension and being disposed substantially midway along the interior axial dimension, wherein the exterior surface walls of the transport wells include exterior rounded ends and the exterior surface walls of the transport wells between the flat surface and the ends of the wells are reduced and tapered relative to the exterior surface walls between the opening of the wells and the flat surfaces, wherein the sample segment can be directly engaged by the transport means by each bore receiving one of said transport wells having said exterior flat surfaces with the corresponding flat surface being directly engaged by the transport means;

a raised boss on the upwardly facing body surface around the opening of one of the wells;

a mixing element disposed within said one of the wells, and a cover applied over and sealed to the boss.

26. A sample segment as in claim 25 wherein the sample segment further includes a plurality of raised bosses on the upwardly facing body surface around selected ones of the wells.

27. A sample segment as in claim 26 wherein the sample segment includes curved opposite edges and the wells are formed in an arc between the curved opposite edges.

28. A sample segment as in claim 27 wherein the segment further includes raised arcuate ribs proximate the curved opposite edges, and a cover that is applied over the ribs and bosses and is sealed to the bosses.

29. A sample segment as is claim 25 wherein the annular flat surfaces of said transport wells are disposed on the exterior walls of the transport wells such that, for each of said transport wells, most of the interior volume of the well is between a plane defined by the flat surface and the opening of the well.

30. A sample segment for use with an automated analyzer having transport means comprising an arm and at least two bores, the sample segment comprising:

a body having an upwardly facing surface and a downwardly facing surface;

a plurality of wells integrally formed as inseparable components of the body, each of the wells having an opening in an upwardly facing surface of the body and defining an interior volume, at least two of the wells being transport wells and having an interior axial dimension defined by exterior surface walls and including exterior annular flat surfaces around the exterior walls of said transport wells, the flat surfaces facing downwardly in a direction parallel to said axial dimension and being disposed substantially midway along the interior axial dimension, wherein the exterior surface walls of the transport wells include exterior rounded ends and the exterior surface walls of the transport wells between the flat surface and the ends of the wells are reduced and tapered relative to the exterior surface walls between the opening of the wells and the flat surfaces, wherein the sample segment can be directly engaged by the transport means by each bore receiving one of said transport wells having said exterior flat surfaces with the corresponding flat surface being directly engaged by the transport means;

at least two of the wells containing a reagent;

a mixing element disposed in at least one of the wells containing the reagents; and a cover sealed to the body for retaining the reagents and mixing elements in their respective wells before adding a sample to the wells.

31. A sample segment as in claim 30 wherein the mixing element is a length of wire.

32. A sample segment as in claim 31 wherein the wire is nickel chromium.

33. A sample segment for use with an automated analyzer having transport means comprising an arm and at least two bores, the sample segment comprising:

a body having an upwardly facing surface and a downwardly facing surface;

a plurality of wells integrally formed as inseparable components of the body, each of the wells having an opening in an upwardly facing surface of the body and defining an interior volume, at least two of the wells being transport wells and having an interior axial dimension defined by exterior surface walls and including exterior annular flat surfaces around the exterior walls of said transport wells, the flat surfaces facing downwardly in a direction parallel to said axial dimension and being disposed substantially midway along the interior axial dimension, wherein the exterior surface walls of the transport wells include exterior rounded ends and the exterior surface walls of the transport wells between the flat surface and the ends of the wells are reduced and tapered relative to the exterior surface walls between the opening of the wells and the flat surfaces, wherein the sample segment can be directly engaged by the transport means by each bore receiving one of said transport wells having said exterior flat surfaces with the corresponding flat surface being directly engaged by the transport means;

at least two of the wells containing a reagent;

a mixing element disposed in at least one of the wells containing the reagents; and a plurality of raised annular bosses on the upwardly facing body surface around the opening of the wells containing the reagents.

34. A sample segment as in claim 33 wherein the reagents in the wells are different.

35. A sample segment as in claim 34 wherein the reagents in the wells are adapted for immunosubtraction.

36. A sample segment as in claim 33 comprising, in addition, a cover applied over and sealed to the bosses for closing the wells.

37. A sample segment for use with an automated analyzer having transport means comprising an arm and at least two bores, the sample segment comprising:

a body having an upwardly facing surface and a downwardly facing surface;

a plurality of wells integrally formed as inseparable components of the body, each of the wells having an opening in an upwardly facing surface of the body and defining an interior volume, at least two of the wells being transport wells and having an interior axial dimension defined by exterior surface walls and including exterior annular flat surfaces around the exterior walls of said transport wells, the flat surfaces facing downwardly in a direction parallel to said axial dimension and being disposed substantially midway along the interior axial dimension, wherein the exterior surface walls of the transport wells include exterior rounded ends and the exterior surface walls of the transport wells between the flat surface and the ends of the wells are reduced and tapered relative to the exterior surface walls between the opening of the wells and the flat surfaces, wherein the sample segment can be directly engaged by the transport means by each bore receiving one of said transport wells having said exterior flat surfaces with the corresponding flat surface being directly engaged by the transport means;

at least two wells containing a reagent;

a mixing element disposed in the wells containing the reagent;

raised annular bosses on the upwardly facing body surface around the openings of the wells containing the reagent; and a cover applied over and sealed to the bosses for closing the wells.

38. The sample segment of claim 37 wherein the cover is a label.

39. A sample segment as in claim 38 wherein the label includes readable characters thereon.

40. The sample segment of claim 37 wherein the reagent includes a liquid component and a solid support component.

41. A reagent segment useful with an automated analyzer having transport means comprising an arm, at least two bores and vacuum means for controllably applying a vacuum to the bores, the reagent segment comprising:

a curved body having an upwardly facing surface and a downwardly facing surface;

a plurality of wells integrally formed as inseparable components of the body, each of the wells having an opening in an upwardly facing surface of the body, interior tapered walls, and a rounded bottom, at least two of the wells being transport wells and having an interior axial dimension defined by exterior surface walls and including exterior annular flat surfaces formed around the exterior walls of said transport wells, the flat surfaces facing downwardly in a direction parallel to said axial dimension and being disposed substantially midway along the interior axial dimension, wherein the exterior surface walls of the transport wells include exterior rounded ends and the exterior surface walls of the transport wells between the flat surface and the ends of the wells are reduced and tapered relative to the exterior surface walls between the opening of the wells and the flat surfaces, wherein the reagent segment can be directly engaged by the transport means by each bore receiving one of said exterior flat surfaces with the corresponding flat surface being directly engaged by the transport means;

a reagent disposed in selected ones of the wells;

a free mixing element disposed in at least one of wells in which the reagent is disposed;

a plurality of raised annular bosses formed around the openings of the wells in the upwardly facing surface;

raised arcuate portions proximate edges of the upwardly facing surface; and a cover affixed to the upwardly facing surface and sealed to the raised annular bosses.

42. A sample segment for use with an automated analyzer having transport means comprising an arm and at least two bores, the sample segment comprising:

a body having an upwardly facing surface and a downwardly facing surface; and a plurality of wells integrally formed as inseparable components of the body, at least two of the wells being transport wells and having an interior axial dimension defined by exterior surface walls and including exterior annular flat surfaces around the exterior walls of said transport wells, the flat surfaces facing downwardly in a direction parallel to said axial dimension and being disposed substantially midway along the interior axial dimension, the transport wells including inner tapered walls and exterior surface walls wherein the exterior surface walls include exterior rounded ends, and the exterior surface walls of the transport wells between the flat surface and the ends of the wells are reduced and tapered relative to the exterior surface walls between the opening of the wells and the flat surfaces, wherein the sample segment can be directly engaged by the transport means by each bore receiving one of said transport wells with the corresponding flat surface being directly engaged by the transport means.

* * * * *